(12) United States Patent
Visel et al.

(10) Patent No.: US 8,701,534 B2
(45) Date of Patent: Apr. 22, 2014

(54) MACHINE TOOL

(75) Inventors: Benjamin Visel, Schwieberdingen (DE); Georg Stellmann, Ludwigsburg (DE); Joachim Platzer, Remseck-Hochberg (DE); Sebastian Jackisch, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 152 days.

(21) Appl. No.: 12/733,764

(22) PCT Filed: Jul. 22, 2008

(86) PCT No.: PCT/EP2008/059556
§ 371 (c)(1),
(2), (4) Date: Aug. 16, 2010

(87) PCT Pub. No.: WO2009/040153
PCT Pub. Date: Apr. 2, 2009

(65) Prior Publication Data
US 2011/0277609 A1    Nov. 17, 2011

(30) Foreign Application Priority Data
Sep. 20, 2007  (DE) .......................... 10 2007 044 800

(51) Int. Cl.
*B23D 45/04*  (2006.01)
*B23Q 17/24*  (2006.01)

(52) U.S. Cl.
USPC .................. 83/365; 83/58; 83/62.1; 83/471.2

(58) Field of Classification Search
USPC .......... 83/58, 62.1, 561, 47, 63, 74, 469, 788, 83/DIG. 1, 477.2, 477.1, 490, 589, 471.3, 83/397.1, 365, 471.2, 644; 144/382, 427; 173/1; 700/21, 171, 108; 702/65; 340/686.5, 411; 307/117; 241/37.5; 356/445; 424/9.5, 9.6; 250/342, 250/339.07, 388.1; 361/181, 281, 286, 176; 320/166, 562, 658, 663, 665–668, 675, 320/686, 688, 698
See application file for complete search history.

(56) References Cited

U.S. PATENT DOCUMENTS

| | | | |
|---|---|---|---|
| 4,500,784 A | | 2/1985 | Hacskaylo |
| 4,710,629 A | * | 12/1987 | Muller et al. ................. 250/342 |
| 5,400,784 A | | 3/1995 | Durand et al. |
| 6,818,893 B2 | * | 11/2004 | Carter ....................... 250/339.07 |
| 7,353,737 B2 | * | 4/2008 | Gass et al. ..................... 83/62.1 |
| 2004/0194594 A1 | * | 10/2004 | Dils et al. ........................ 83/13 |
| 2004/0226424 A1 | | 11/2004 | O'Banion et al. |
| 2006/0101960 A1 | * | 5/2006 | Smith et al. ...................... 83/58 |
| 2008/0185525 A1 | * | 8/2008 | Lyubchik et al. ............. 250/342 |
| 2010/0037739 A1 | * | 2/2010 | Anderson et al. ................ 83/58 |
| 2010/0236663 A1 | * | 9/2010 | Gass ............................. 144/329 |

FOREIGN PATENT DOCUMENTS

| | | |
|---|---|---|
| CN | 1717563 | 1/2006 |
| CN | 101028719 | 9/2007 |
| EP | 1 182 425 | 2/2002 |
| JP | 3-123660 | 12/1991 |

(Continued)

*Primary Examiner* — Ghassem Alie
(74) *Attorney, Agent, or Firm* — Kenyon & Kenyon LLP

(57) ABSTRACT

A machine tool, in particular a sawing machine, is described, having a work surface (14) for placing a workpiece (16) to be machined and a tool support unit (20) for supporting a tool (18), the tool support unit being supported movably relative to the work surface (14). The machine tool includes a tool operation monitoring device (60) for monitoring a tool range (68) at least during tool operation, the device having an imaging unit (62).

13 Claims, 7 Drawing Sheets

(56) References Cited

FOREIGN PATENT DOCUMENTS

| | | |
|---|---|---|
| JP | 11-99449 | 4/1999 |
| JP | 2002-525211 | 8/2002 |
| JP | 2002-263989 | 9/2002 |
| JP | 2004-160822 | 6/2004 |
| RU | 1607204 | 3/1993 |
| RU | 2131335 | 6/1999 |
| WO | WO 00/16036 | 3/2000 |

* cited by examiner

|     | $V_1$ | $V_2$ | $V_3$ | $V_4$ |
|-----|-------|-------|-------|-------|
| $A_1$ | T | F | F | T |
| $A_2$ | F | T | T | F |
| $A_3$ | F | F | T | T |
| ⋮   | ⋮ | ⋮ | ⋮ | ⋮ |

|     | $V_1/V_2$ | $V_1/V_3$ | $V_1/V_4$ | $V_2/V_3$ |
|-----|-----------|-----------|-----------|-----------|
| $A_1$ | F | T | T | F |
| $A_2$ | T | F | F | F |
| $A_3$ | F | T | T | T |
| ⋮   | ⋮ | ⋮ | ⋮ | ⋮ |

↙ 100

MACHINE TOOL

BACKGROUND OF THE INVENTION

1. Field of the Invention

The present invention is directed to a machine tool.

2. Description of Related Art

A miter saw is known which has a workbench, a support unit for rotational support of a saw blade, and a lowerable arm which may be actuated by an operator for moving the support unit relative to the workbench.

BRIEF SUMMARY OF THE INVENTION

The present invention is directed to a machine tool, e.g., a sawing machine, having a work surface for placing a workpiece to be machined, and a tool support unit for supporting a tool which is supported movably relative to the work surface.

It is proposed that the machine tool has a recognition unit which is provided for detecting the presence of a type of material in a tool range with the aid of spectral evaluation of radiation. In this manner it is possible to achieve reliable and rapid recognition of an application situation for a machine tool, in particular when the tool support unit moves relative to the work surface. In the present context, a "tool range" refers in particular to a range composed of points having a minimum distance of 10 cm maximum, advantageously 5 cm maximum, and preferably 2 cm maximum, from a tool and/or a tool extension range of the machine tool. A "tool extension range" is composed in particular of points which may potentially be occupied by a tool, in particular due to the movable support of the tool support unit for supporting the tool relative to the machine tool work surface. The imaging unit has a field of vision which during operation advantageously establishes a monitored range of the machine tool. The monitored range preferably includes at least a portion of the tool range. The vertical projection of the monitored range on the work surface advantageously includes the vertical projection of the tool range on the work surface. The monitored range may also include at least one partial range of the tool extension range.

It is further proposed that the recognition unit is provided for detecting the presence in particular of a human body part in the tool range. This may be achieved by recognizing a human tissue and/or a material worn by the operator. "Radiation" refers in particular to electromagnetic radiation. A "spectrum" of radiation refers in particular to a distribution of a radiation parameter, in particular the intensity of the radiation, as a function of the wavelength, frequency, and/or time. Furthermore, "spectral evaluation" of radiation refers in particular to signal evaluation in which a result is evaluated by detecting a characteristic of a spectrum of the radiation, such as, for example, an intensity integrated over the wavelength. It is further proposed that the recognition unit has at least one sensor means, and the machine tool has a carrier means which is used to carry along the sensor means in a motion of the tool support unit relative to the work surface. A high level of safety may thus be achieved when the tool support unit moves.

In one example embodiment of the present invention, it is proposed that the tool support unit is provided for rotationally supporting a tool in a plane of rotation, and the recognition unit has a sensor means situated laterally to the plane of rotation. A system situated "laterally" to the plane of rotation refers in particular to a system in a half-space which is delimited by the plane of rotation. Complete embedding in this half-space is to be understood in particular. A "plane of rotation" refers in particular to a plane which contains the center of gravity of the tool and is oriented perpendicular to a rotational axis of the tool. It is particularly advantageous for the sensor means to be situated laterally to the tool. The projection of the sensor means on the tool perpendicular to the plane of rotation is embedded in a tool surface.

In one advantageous refinement of the present invention, it is proposed that the machine tool has a safety means which is provided to prevent a motion of the tool support unit relative to the work surface on the basis of a signal of the recognition unit, so that contact of a supported tool with an undesired object or human body part present in a tool extension range may advantageously be avoided.

The recognition unit is advantageously provided for presence recognition by evaluating a reflection spectrum of radiation reflected on an object to be examined, thus allowing effective recognition of the type of material based on contrast detection.

In one example embodiment of the present invention, it is proposed that the recognition unit has a sensor unit having at least one sensitivity range for detecting radiation in a wavelength range which is at least partially in the infrared spectrum, thus allowing reliable and rapid recognition to be achieved in a particularly economical manner.

Alternatively or additionally, the recognition unit may have a signal unit which is provided for ultrabroadband operation. A signal unit which is provided for ultrabroadband operation is understood in particular to mean a unit which allows an ultrabroadband signal to be generated, received, and/or evaluated. An "ultrabroadband signal" refers in particular to a signal having a frequency spectrum with a center frequency and a frequency bandwidth of at least 500 MHz. The center frequency is preferably selected to be in the frequency range of 1 GHz to 15 GHz.

Particularly reliable recognition may be achieved when the wavelength range is a mid-near infrared range. In this manner a sensitivity range may be provided which is tailored in a targeted manner to the detection and evaluation of a reflection spectrum. In the present context, "mid-near infrared range" refers in particular to a wavelength interval of the infrared spectrum which is less than a wavelength of 15 μm. In addition, high contrast between human tissue and material may be achieved when the sensitivity range for detecting radiation is provided in a wavelength interval of the infrared spectrum which is less than a wavelength of 8 μm. It is particularly advantageous when the wavelength range is a near infrared range. In the present context, "near infrared range" refers in particular to a wavelength interval of the infrared spectrum which is less than a wavelength of 1.5 μm, such as in particular a wavelength interval in the IR-A range. The wavelength range may also be partially in the visible range of the electromagnetic spectrum.

An evaluation signal having a high signal intensity may be achieved when the recognition unit has a transmitter unit which is provided for transmitting radiation having at least one radiation portion in the wavelength range.

It is further proposed that the transmitter unit is provided for transmitting radiation in the wavelength range and in at least one additional wavelength range, thus allowing the accuracy in a recognition operation to be increased. To differentiate the radiation portions in the various wavelength ranges, these radiation portions may each be transmitted in the form of a pulse, a given pulse length being associated with a given wavelength range. For example, the pulses may be transmitted simultaneously.

An advantageous differentiation may also be achieved when the transmitter unit is provided for transmitting radiation successively in the wavelength range and in at least one additional wavelength range. In this manner radiation may be generated in a targeted manner in desired wavelength ranges, it being possible to dispense with complicated filtering for detection of the radiation by the sensor unit. A high signal-to-noise ratio may also be achieved. "Successive" transmission in two wavelength ranges is understood in particular to mean that the transmission in the first wavelength range and the transmission in the second wavelength range are substantially free of overlap. In this regard an overlap duration in which radiation is simultaneously transmitted in two wavelength ranges should be less than 10%, advantageously less than 5%, and preferably less than 1% of the shortest transmission duration in a wavelength range. It is particularly advantageous for the transmission operations to be free of overlap, separate pulses being emitted by the transmitter unit.

The sensor unit advantageously has at least one further sensitivity range which is provided for detecting radiation in an additional wavelength range, thus allowing a further increase in reliability of the recognition of the type of material. The wavelength ranges may overlap. However, it is advantageous when the wavelength ranges are separate from one another. Particularly accurate recognition may be achieved when the sensor unit has at least three sensitivity ranges, each of which is provided for detecting radiation in a different wavelength range.

In this regard it is proposed that the recognition unit has an evaluation means which is provided for recognizing the presence of the type of material on the basis of a ratio of at least two radiation parameters, each of which is associated with a radiation portion in a different wavelength range. Rapid recognition may be advantageously achieved in this manner. In particular, taking reference radiation into account may be dispensed with. A "radiation parameter" refers in particular to a parameter which is detected on the basis of a radiation incident on the sensor unit. This parameter may in particular be an electrical parameter.

In one example implementation of the present invention, it is proposed that the wavelength range be narrowband. In the present context, a "narrowband wavelength range" refers in particular to a wavelength range which has a bandwidth of 100 nm maximum, advantageously 50 nm maximum, preferably 20 nm maximum, and particularly preferably 10 nm maximum. It is thus possible to advantageously dispense with filtering of detected radiation of a complex design.

DETAILED DESCRIPTION OF THE INVENTION

Figure 1:
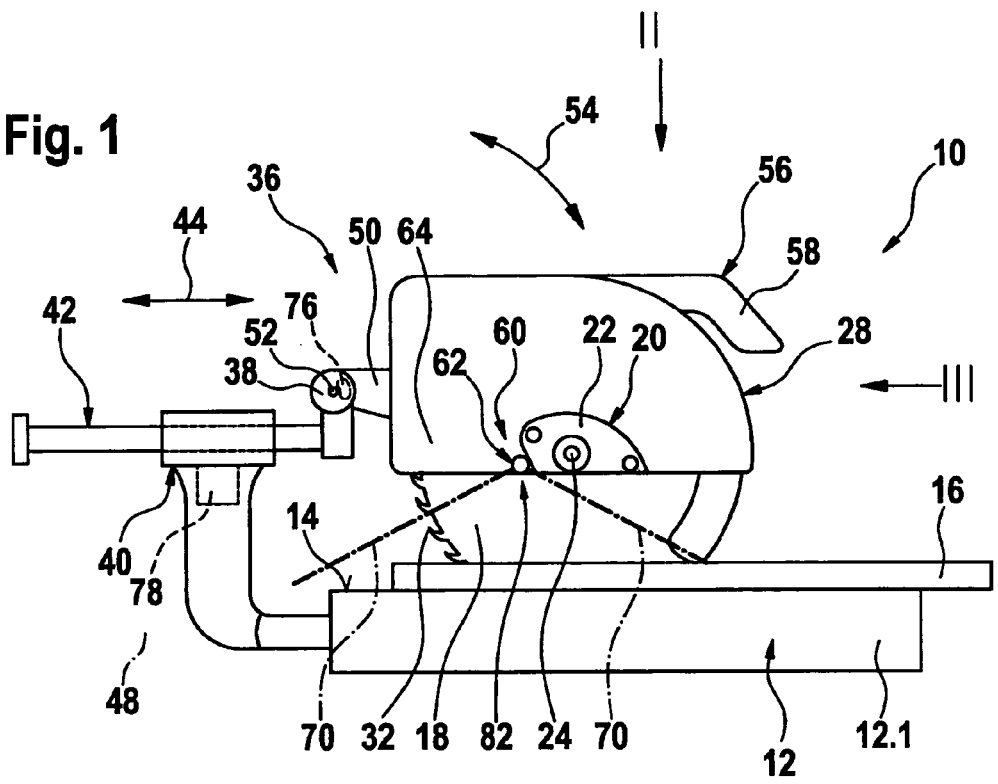
FIG. 1 shows a miter saw having a tool operation monitoring device integrated into a safety cover, in a side view.
Figure 2:
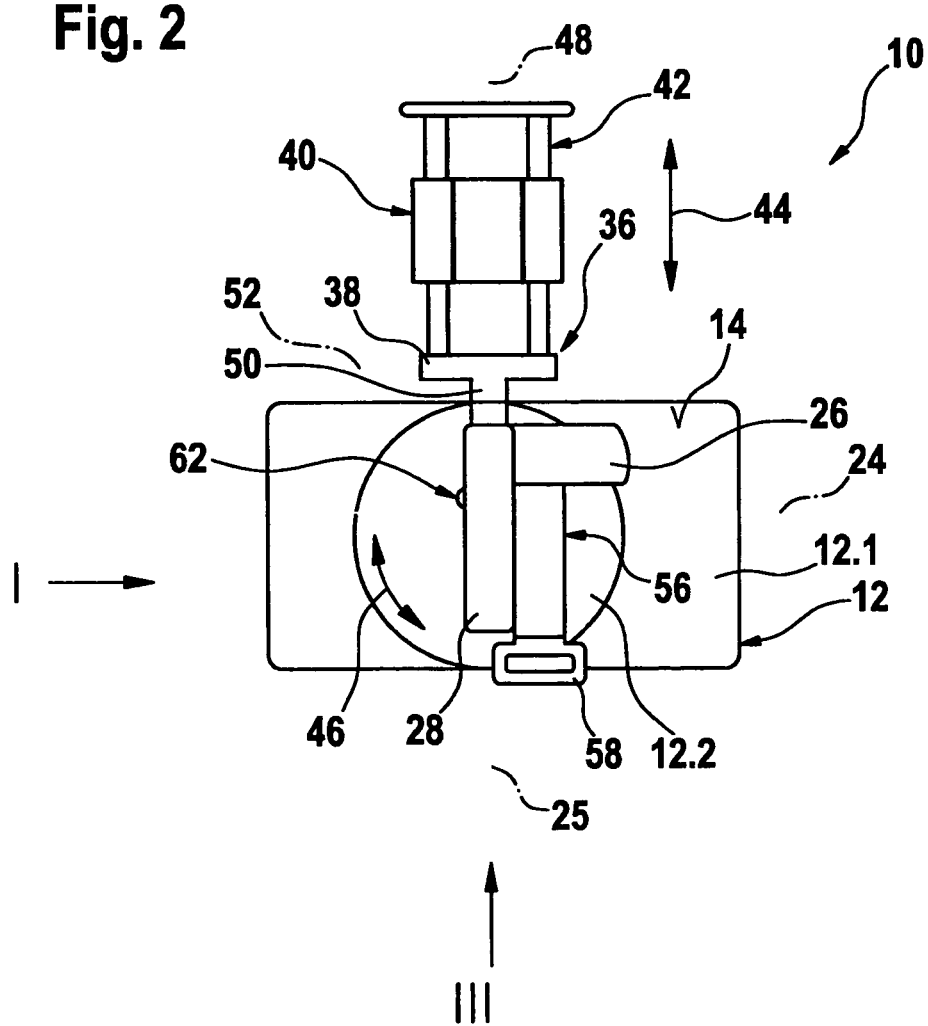
FIG. 2 shows the miter saw from FIG. 1 in a top view.

FIG. 1 shows a machine tool 10 designed as a stationary device, in particular as a miter saw, in a side view. The following description also refers to FIG. 2, which illustrates machine tool 10 from FIG. 1 in a top view. Machine tool 10 may also be designed as a compound miter saw or crosscut saw. Machine tool 10 has a workbench 12 which forms a work surface 14 which is provided for placing, for example laying or mounting, a workpiece to be machined with the aid of machine tool 10. As shown in FIG. 2, workbench 12 has a first component 12.1, which is fixedly connected to a stop area or support device (not illustrated in detail) for stopping or supporting workbench 12, and a second, circular component 12.2 which is supported rotatably relative to component 12.1 about an axis perpendicular to work surface 14. In FIG. 1 a workpiece 16, in the form of a wooden board, to be sawn is placed on work surface 14. When workpiece 16 is machined, machine tool 10 includes a tool 18 designed as a circular saw blade. A tool support unit 20 for machine tool 10 is provided for supporting tool 18. Tool support unit 20 has support means 22 which is used to support tool 18 rotatably about a rotational axis 24. Tool support unit 20 thus defines a plane of rotation 25 for tool 18 which contains the center of gravity of tool 18 and is perpendicular to rotational axis 24. When workpiece 16 is machined, tool 18 is driven with the aid of a drive unit 26 designed as an electric motor for rotation about rotational axis 24. To protect an operator from contacting tool 18, machine tool 10 is equipped with a protective device 28 provided as a safety cover for covering tool 18, which covers a cutting edge 32 of tool 18 over at least one-half the circumference of the cutting edge. As shown in FIG. 1, tool support unit 20 is fastened to protective device 28. Tool 18, tool support unit 20, drive unit 26, and protective device 28 are components of a tool unit 36 which is supported movably relative to workbench 12 and in particular relative to component 12.1. For this purpose, machine tool 10 has a first support unit 38 which is used to support tool unit 36, in particular tool support unit 20, movably relative to work surface 14, and via which tool support unit 20 is connected to work surface 14. Tool unit 36 may be rotated about a horizontal rotational axis 52, oriented parallel to rotational axis 24, with the aid of support unit 38 and a lowerable arm 50. Thus, tool 18 is supported movably at its rotational axis 24 along a curved path of motion 54 which, starting from a neutral position shown in FIG. 3, leads to the lower working position, shown in FIG. 1, to workpiece 16 to be machined.

Support unit 38 itself is supported movably relative to workbench 12. For this purpose machine tool 10 has a second support unit 40. Support unit 40 is designed as a holding unit which is provided for holding and passing through a guide unit 42. This guide unit 42, which is fixedly connected to support unit 38, is used in cooperation with support unit 40 to guide tool unit 36, in particular tool support unit 20, and support unit 38 relative to work surface 14. This guiding occurs in a linear direction of motion 44 oriented parallel to work surface 14 and perpendicular to rotational axis 52. Support units 38, 40 and tool unit 36 may also be rotated in a rotational direction 46 about an axis which is perpendicular to work surface 14. Support unit 40 itself may be designed to be movable relative to workbench 12, in particular relative to component 12.2. In particular, the support unit is able to perform swivel motions about an axis of inclination 48 which is oriented horizontally and parallel to direction of motion 44, thus enabling tilting motions of tool unit 36 relative to work surface 14.

The motions of tool unit 36 relative to work surface 14 may be actuated by the operator. For this purpose machine tool 10, in particular tool unit 36, is equipped with an actuating unit 56 which is provided for an operator to set tool support unit 20 into motion relative to work surface 14. This actuating unit has a handle 58 which is provided for gripping by one hand of an operator. In this manner the motion of tool unit 36 along horizontal direction of motion 44 and the motion of tool unit 36 about rotational axis 52 along path of motion 54 in the direction of work surface 14, and vice versa, may be actuated by the operator. For operating machine tool 10, the operator grips handle 58 with one hand while typically placing the other hand on workpiece 16. To prevent the hand of an operator from contacting rotating tool 18, machine tool 10 is provided with a tool operation monitoring device 60. This is achieved with the aid of a sensor unit 62, whose operating principle is described below. Sensor unit 62 is fixedly connected to tool unit 36, in particular to tool support unit 20. Sensor unit 62 is fastened to protective device 28. Protective device 28 is used as carrier means 64, which is used to carry along sensor unit 62 during any motion of tool support unit 20 relative to work surface 14.

Figure 3:
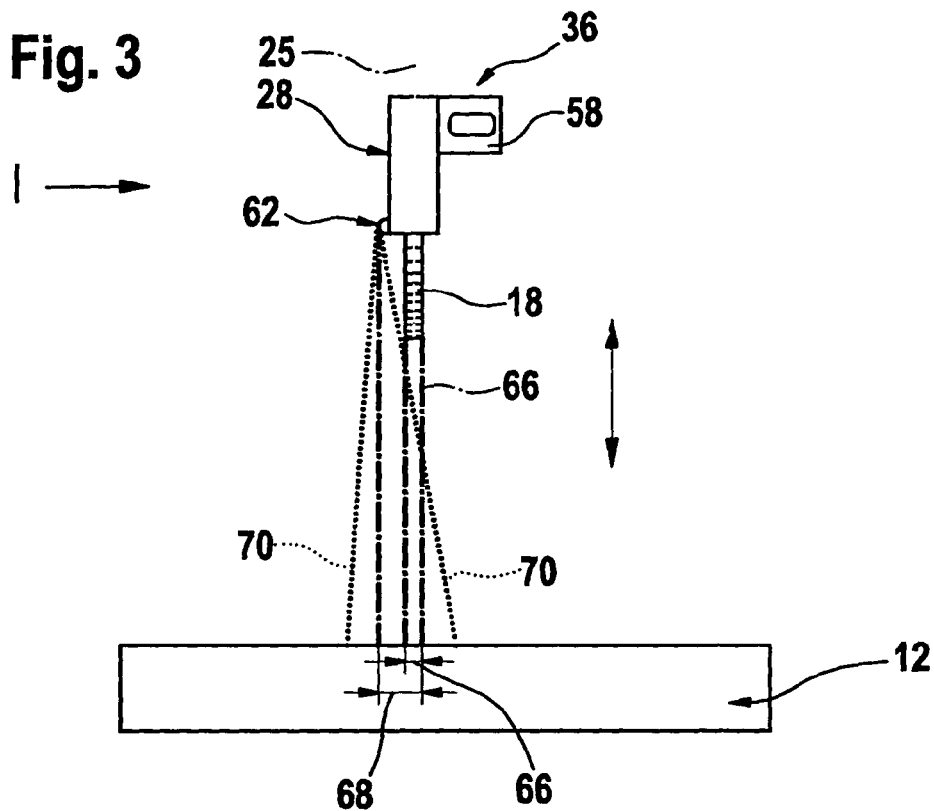
FIG. 3 shows a saw blade and a tool range of the miter saw in a front view.

FIG. 3 shows tool unit 36 in its neutral position, in a front view. The mobility of tool 18 establishes a tool extension range 66 which corresponds to a spatial range which potentially may be occupied by tool 18. Tool extension range 66 is illustrated by vertical dashed-dotted lines. Due to the mobility of tool 18, tool extension range 66 likewise extends in direction of motion 44, in the horizontal direction perpendicular to the plane of the drawing. Tool operation monitoring device 60 is used to monitor a tool range 68. This tool range 68 includes tool extension range 66, and is composed of points having a minimum distance of 2 cm maximum from tool extension range 66. Tool range 68 to be monitored, outside tool extension range 66, is situated laterally to plane of rotation 25, and in particular faces away from actuating unit 56, in particular handle 58, relative to plane of rotation 25. Tool extension range 66 and tool range 68 are schematically delimited by dashed-dotted lines. Sensor unit 62 has a field of vision 70, shown by single-dash lines in Figure (also see FIG. 1), which defines a monitored range of machine tool 10 which includes a significant portion of tool range 68. As shown in FIG. 3, the monitored range may also include a portion of tool extension range 66. For monitoring tool range 68, sensor unit 62 is situated laterally to plane of rotation 25 and tool 18, in particular on a side of plane of rotation 25 facing away from actuating unit 56, in particular facing away from handle 58. Actuating unit 56 and sensor unit 62 are situated on either side of plane of rotation 25.

Figure 4:
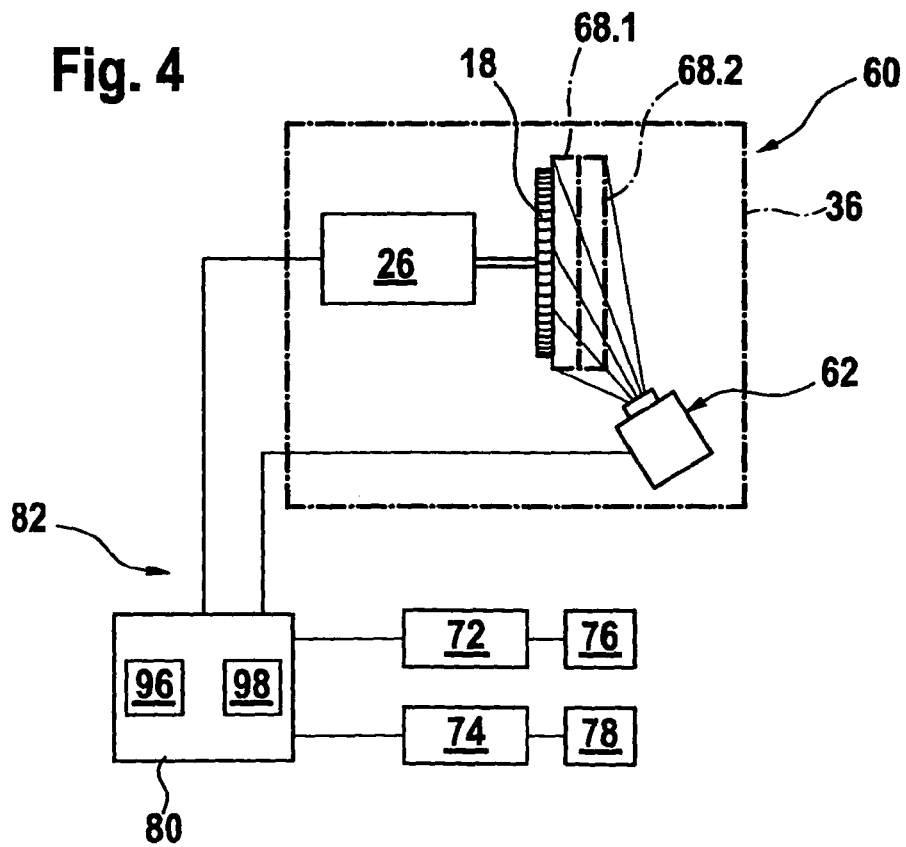
FIG. 4 shows a recognition unit having a sensor unit, an evaluation unit, and safety means for blocking a motion of the saw blade.

FIG. 4 shows a schematic view of a circuit for machine tool 10. Machine tool 10 has actuator units 72, 74 which are provided for carrying out safety measures in cooperation with tool operation monitoring device 60. Actuator units 72, 74 are provided for actuating safety means 76 and 78, respectively. Safety means 76, schematically illustrated in FIG. 1, is a blocking means designed as a clamping means, and is situated in the region of rotational axis 52. Safety means 76 may also be designed as a toothed gear. Safety means 76 is situated in particular in support unit 38. Safety means 76 is used for preventing a rotational motion of tool unit 36, actuated by the operator, about rotational axis 52, i.e., a motion of tool 18 along path of motion 54. Safety means 76 is spring-loaded in a position which enables this motion. This may be achieved, for example, with the aid of a mechanical spring and/or a pull solenoid. Actuator unit 72 is used to bring safety means 76, starting from this position which enables the motion, to a blocking position which blocks the motion, and to actuate a return of safety means 76 to its enabling position. Safety means 78, likewise schematically illustrated in FIG. 1, is situated in support unit 40. Safety means is used to prevent a translational motion of tool unit 36, actuated by the operator, along direction of motion 44. Safety means 78 is likewise a blocking means designed as a clamping means, a wedge element, and/or locking means, for example a locking pin, and may be actuated with the aid of actuator unit 74 for preventing guide unit 42 from advancing. In this regard, reference is made to the description of safety means 76.

Actuator units 72, 74 trigger an actuation of safety means 76 and 78, respectively, as a function of a signal of tool operation monitoring device 60, in particular, a signal of an evaluation unit 80 for tool operation monitoring device 60. In cooperation with sensor unit 62, evaluation unit 80 forms a recognition unit 82 which is provided for recognizing the presence of human tissue in tool range 68. If recognition unit 82 recognizes the presence of human tissue in tool range 68, an actuating signal is transmitted to an actuator unit 72 and/or 74, which on the basis of this actuating signal triggers the above-described blocking of a motion of tool support unit 20 relative to work surface 14. For this purpose evaluation unit 80 is operatively linked to actuator units 72, 74. In addition, a drive of tool 18 may be braked or stopped as a function of such an actuating signal. For this purpose evaluation unit 80 is operatively linked to drive unit 26. Alternatively or additionally, a further actuator unit which is used for braking tool 18 may be provided in conjunction with evaluation unit 80. This actuator unit may actuate a safety means, which is designed as a brake disk or drum brake, for example, and is connected to a shaft (not shown) which is situated in tool support unit 20 and driven by drive unit 26 to rotate tool 18 about rotational axis 24.

It is further proposed, as shown in the design according to FIG. 4, that tool range 68 monitored by sensor unit 62 be subdivided into multiple mode ranges, each of which is associated with a particular safety mode. Thus, for example, tool range 68 may be subdivided into a hazard range 68.1, in which the safety modes described above may be activated, and a warning range 68.2. This warning range 68.2 preferably adjoins hazard range 68.1, is situated on plane of rotation 25 in the direction of rotational axis 24, in front of hazard range 68.1, and has an extension of 1 cm, for example, in this direction. If recognition unit 82 recognizes the presence of a human body part in warning range 68.2, evaluation unit 80 triggers a warning signal to warn the operator. This warning may be provided optically or acoustically, or may be provided with the aid of the above-described blocking using safety means 76 and/or 78, while braking or stopping of a tool drive occurs only when the presence of a human body part is recognized in hazard range 68.1.

Figure 5:
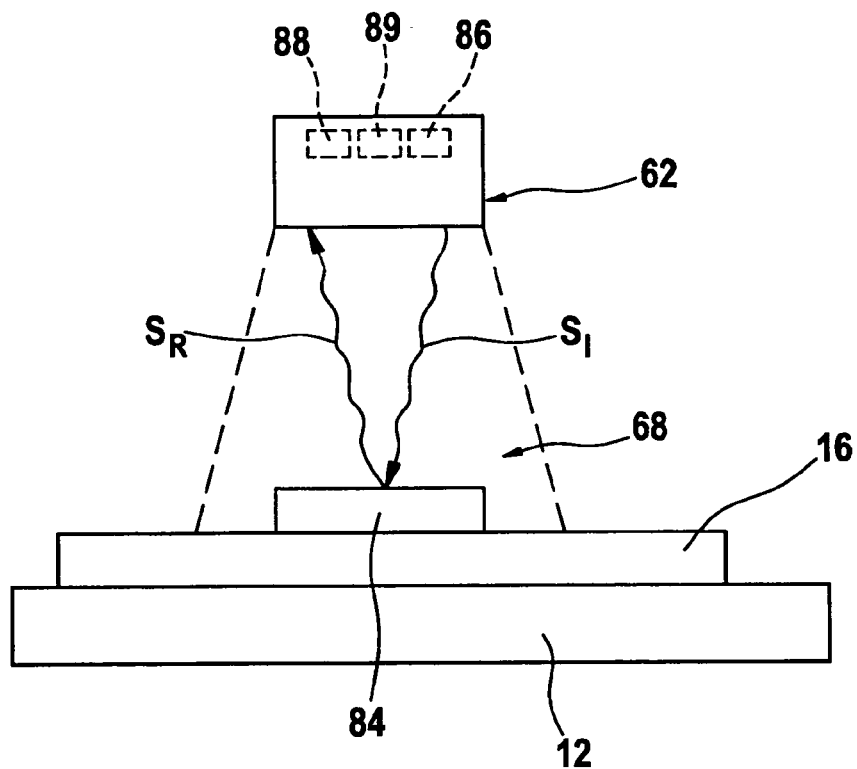
FIG. 5 shows a schematic view of the sensor unit together with a transmitter unit for transmitting radiation.

The functional principle of recognition unit 82 is described with reference to FIG. 5. Work bench 12, workpiece 16, and sensor unit 62 are illustrated in a schematic view. The illustration of tool 18 and protective device 28 is omitted for the sake of clarity. An object to be examined 84 is situated on workpiece 16 in tool range 68. This may in particular be a hand of an operator, some other interfering object, or merely the surface of workpiece 16. Sensor unit 62 has a transmitter unit 86 which during operation transmits radiation $S_I$ into tool range 68. This radiation $S_I$ is reflected on object to be examined 84 and is received as radiation $S_R$ by a receiver unit 88 of sensor unit 62, schematically illustrated in the figure. Sensor unit 62 also has a marking unit 89 for marking tool range 68.

Figure 6:
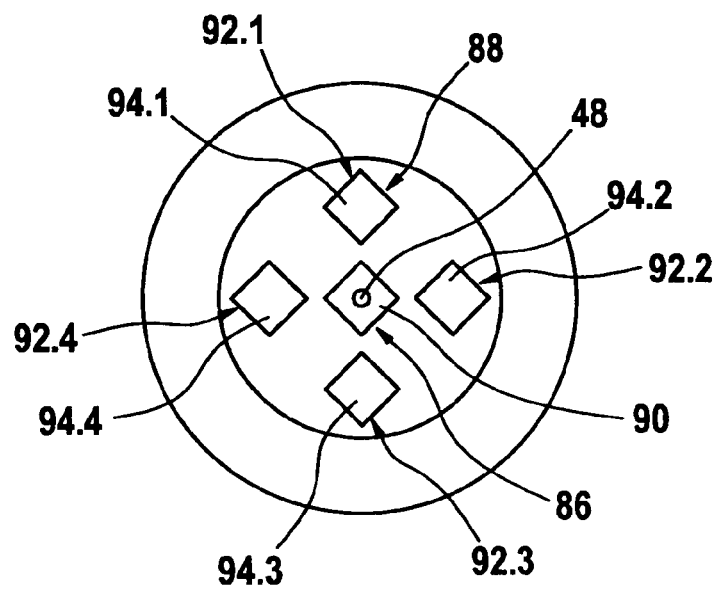
FIG. 6 shows the sensor unit in a front view.

FIG. 6 shows transmitter unit 86 and receiver unit 88 of sensor unit 62 in a front view in which the optical axis of the system intersects the plane of the drawing. Transmitter unit 86 has transmission means 90 designed as an LED. Four sensor means 92 for receiver unit 88, each designed as a photodiode, are situated in the direct vicinity of transmission means 90.

Figure 7:
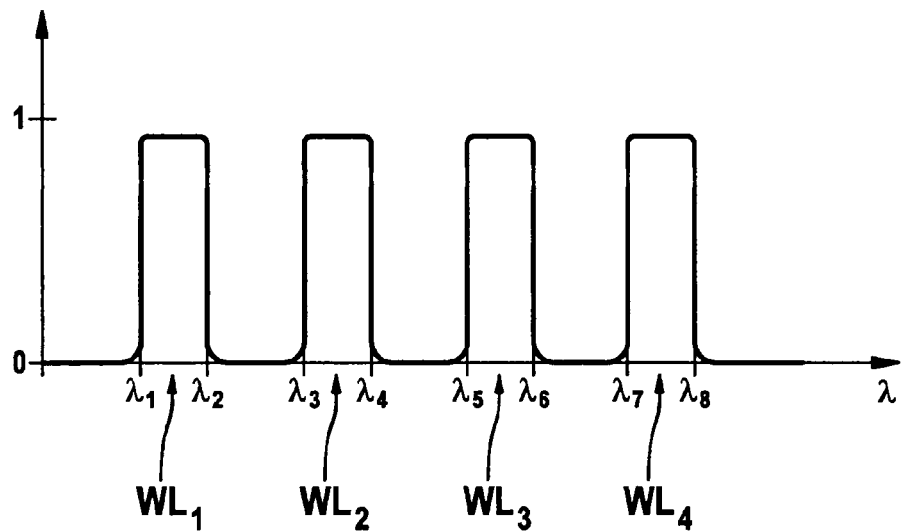
FIG. 7 shows the variation over time of the transmission factor of a receiver unit for the sensor unit as a function of the wavelength.

Each sensor means 92 has a sensitivity range 94 which is provided for detecting radiation in a different wavelength range $WL_1=[\lambda_1, \lambda_2]$, $WL_2=[\lambda_3, \lambda_4]$, $WL_3=[\lambda_5, \lambda_6]$, and $WL_4=[\lambda_7, \lambda_8]$. This is schematically illustrated in FIG. 7. FIG. 7 shows the variation over time of the transmission factor for receiver unit 88 as a function of wavelength $\lambda$ of received radiation $S_R$ received by receiver unit 88. In the exemplary embodiment under discussion, wavelength ranges $WL_i$ are provided without mutual overlap. Wavelength ranges $WL_i$ have, for example, a central wavelength of 630 nm, 700 nm, 980 nm, 1050 nm, and 1200 nm, and are provided as narrowband, each with a bandwidth of approximately 10 nm. For narrowband filtering of detected radiation $S_R$, in addition to sensor means 92 receiver unit 88 may be provided with a system of filter components provided upstream from sensor means 92. For the design of sensor means 92 as selective photodiodes, narrowband filtering is inherent to the system, so that additional filter components may be advantageously avoided. Alternatively or additionally to photodiodes, sensor means 92 may be designed as CCD or CMOS fields, InGaAs detectors, pyroelectric detectors, etc.

Wavelength ranges $WL_2$, $WL_3$, $WL_4$ are present in the infrared spectrum. In particular, these wavelength ranges $WL_2$, $WL_3$, $WL_4$ are each ranges in the near infrared spectrum IR-A having limit values of [700 nm, 1400 nm]. Wavelength range $WL_1$ is present, at least partially, in the visible range of the electromagnetic spectrum. Alternatively or additionally, wavelength ranges may be selected in the infrared ranges IR-B (1.4-3 μm) and IR-C (3-15 μm). Transmitter unit 86 together with transmission means 90 generates radiation which includes wavelength ranges $WL_i$ shown in FIG. 7.

Figure 8:
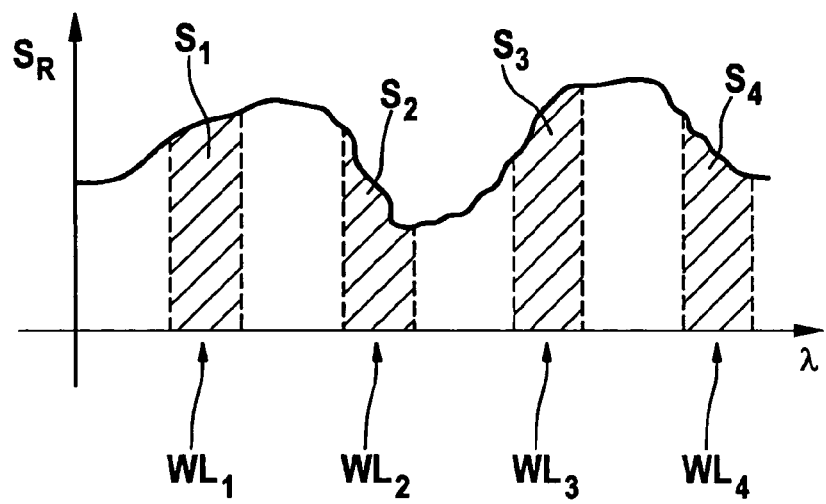
FIG. 8 shows the reflection spectrum of radiation reflected on the reflecting object as a function of the wavelength.

The principle of recognition of the presence of human tissue in tool range 68 is explained with reference to FIGS. 8, 9, and 10. FIG. 8 shows the reflection spectrum of radiation $S_R$ reflected on object to be examined 84 and detected by sensor means 92. This reflection spectrum corresponds to the distribution of the signal intensity as a function of wavelength $\lambda$ of radiation $S_R$. Each sensor means 92 or sensitivity range 94 detects a portion of the reflection spectrum in corresponding wavelength ranges $WL_i$. At its output terminal, sensor means 92 generate a radiation parameter $V_i$, provided in each case as electrical voltage. Radiation parameter $V_1$, for example, is proportional to a signal intensity $s_1$ of radiation $S_R$ integrated over wavelength range $WL_1$, and indicated by crosshatched lines in FIG. 8.

Figures 9, 10:
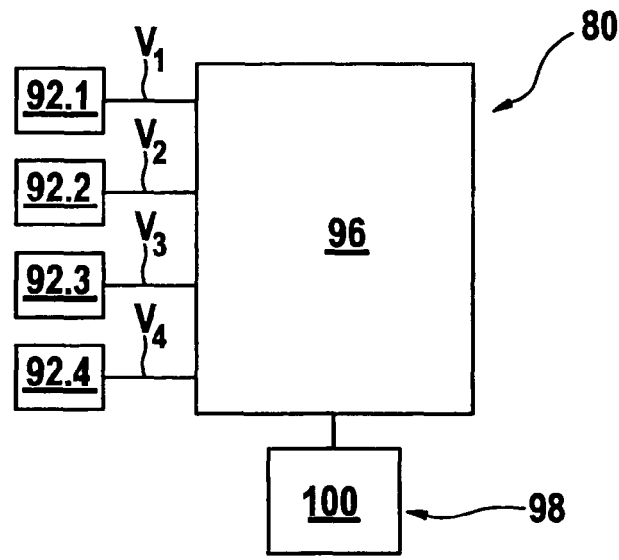
FIG. 9 shows an internal circuit of the recognition unit.
FIG. 10 shows a database stored in the recognition unit.

As shown in FIG. 9, radiation parameters $V_i$ are provided to an input of evaluation means 96, for example a microprocessor, of evaluation unit 80. In a further variant it is possible to amplify radiation parameters $V_i$. For evaluation, radiation parameters $V_i$ are compared to values in a database 100 stored in a memory unit 98 of evaluation unit 80 with the aid of logical operations. This database 100 is schematically illustrated in FIG. 10. In a first evaluation strategy, detected radiation parameters $V_i$ are compared to stored values $A_1, A_2, A_3$, etc. A recognition variable which may assume the values "False" (F) or "True" (T) is associated with each pair $(V_i, \lambda_i)$. For value "F" the presence of human tissue in tool range 68 is ruled out. In a second alternative or additional evaluation strategy, evaluation means 96 determines ratios $V_1/V_2$, $V_1/V_3$, etc., among the various radiation parameters $V_i$. These ratios are compared to stored values $A_1, A_2, A_3$, etc., thus allowing, as described above, conclusions to be drawn concerning the presence of human tissue in tool range 68. A recognition which is independent of intensity may be carried out by forming ratios. Information concerning the spectral sensitivity of sensor means 92 which may be used for evaluating radiation parameters $V_i$ may also be stored in memory unit 98.

Figure 11:
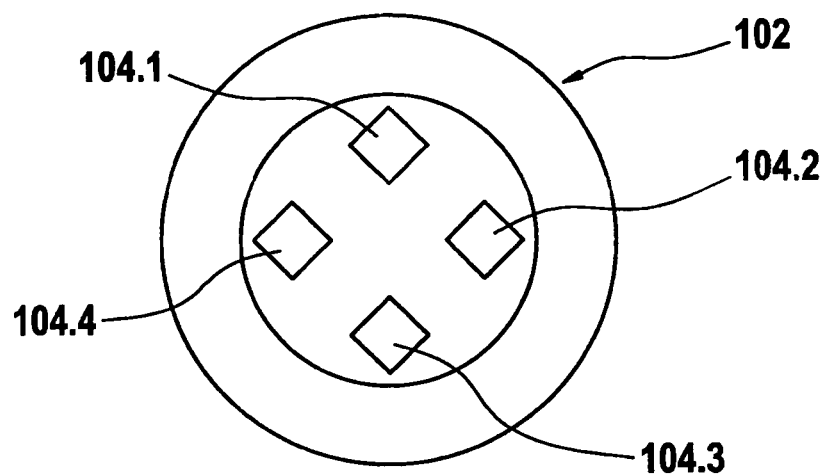
FIG. 11 shows an alternative transmitter unit of the sensor unit for generating pulses.
Figure 12:
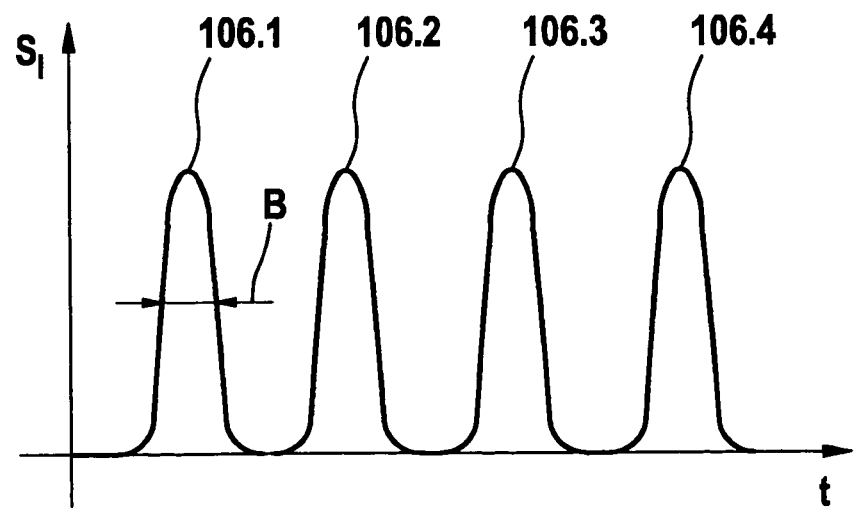
FIG. 12 shows the intensity of radiation generated by the transmitter unit from FIG. 11.

In one alternative design variant shown in FIGS. 11 and 12, sensor unit 62 is provided with a transmitter unit 102 which has at least two, in particular at least three, and particularly preferably at least four, transmission means 104.1 through 104.4 for transmitting the radiation in each of different wavelength ranges $WL_1$ through $WL_4$ which are successively operated during operation of transmitter unit 102. FIG. 9 shows transmitter unit 102 which generates radiation $S_f$, which contains a series of pulses 106.1 through 106.4 as illustrated in FIG. 12. FIG. 12 shows the variation of the intensity of radiation $S_f$ as a function of time t. A pulse 106 has a width B of approximately 100 μs. Transmitter unit 102 is provided for transmitting radiation successively in wavelength ranges $WL_1$ through $WL_4$. In a sequence of four consecutive pulses 106.1 through 106.4 the pulses are each associated with a different wavelength range $WL_1$ through $WL_4$. Transmission means 104 may be designed as LEDs, for example. As the result of such successive radiation in various wavelength ranges $WL_i$, complicated filtering of detected reflected radiation $S_R$ may be dispensed with.

What is claimed is:

1. A machine tool configured as a sawing machine, comprising:
   a work surface configured to support a workpiece to be machined;
   a tool-support unit for supporting a rotation of a tool about a first rotational axis and an arcing of the tool about a second rotational axis relative to the work surface;
   a recognition unit configured to detect, with the aid of spectral evaluation of radiation, the presence of a selected type of one of a material and a human tissue in a tool range as the tool is rotated about the first rotational axis and arced about the second rotational axis,
   wherein the recognition unit has a transmitter configured to transmit radiation having at least one radiation portion in the wavelength range which is at least partially in the infrared spectrum,
   wherein the transmitter unit is configured to transmit radiation in at least one additional wavelength range, and
   wherein the transmitter unit is configured to transmit radiation successively in a) the wavelength range which is at least partially in the infrared spectrum and (b) in the at least one additional wavelength range.

2. The machine tool as recited in claim 1, further comprising:
   a carrier unit;
   wherein the recognition unit includes at least one sensor unit, and wherein the carrier unit is configured to transport the at least one sensor unit in a motion of the tool-support unit relative to the work surface.

3. The machine tool as recited in claim 2, wherein the tool-support unit is configured to provide a rotational support for the tool in a plane of rotation, and wherein the sensor unit of the recognition unit is situated laterally to the plane of rotation.

4. The machine tool as recited in claim 2, further comprising:

a safety unit configured to prevent, on the basis of a signal of the recognition unit, a motion of the tool-support unit relative to the work surface.

5. The machine tool as recited in claim 2, wherein the recognition unit is configured to detect the presence of the selected type of the one of the material and the human tissue in a tool range by evaluating a reflection spectrum of radiation reflected from a target object.

6. The machine tool as recited in claim 5, wherein the at least one sensor unit of the recognition unit has at least one sensitivity range for detecting radiation in a wavelength range which is at least partially in the infrared spectrum.

7. The machine tool as recited in claim 6, wherein the wavelength range which is at least partially in the infrared spectrum is in a mid-near infrared range.

8. The machine tool as recited in claim 6, wherein the at least one sensor unit of the recognition unit has at least one additional sensitivity range which is provided for detecting radiation in an additional wavelength range.

9. The machine tool as recited in claim 8, wherein the recognition unit has evaluation unit configured to recognize the presence of the selected type of the one of the material and the human tissue on the basis of a ratio of at least two radiation parameters which are associated with radiation portions in different wavelength ranges.

10. The machine tool as recited in claim 6, wherein the wavelength range which is at least partially in the infrared spectrum is narrowband.

11. The machine tool as recited in claim 1, wherein the first rotational axis is parallel to the second rotational axis.

12. The machine tool as recited in claim 1, wherein the tool-support unit further supports a linear movement of the tool in a radial direction to the first rotational axis and the recognition unit is configured to detect the presence of the selected type of the one of the material and the human tissue in the tool range as the tool is moved in the radial direction.

13. A machine tool configured as a sawing machine, comprising:
    a work surface configured to support a workpiece to be machined;
    a tool-support unit for supporting a rotation of a tool about a first rotational axis and an arcing of the tool about a second rotational axis relative to the work surface; and
    a recognition unit including at least one sensor and a carrier that carries the sensor along in a motion of the tool-support unit relative to the work surface, the recognition unit configured to detect the presence of a selected type of one of a material and a human tissue in a tool range with the aid of spectral evaluation of radiation data from the sensor as the tool is rotated about the first rotational axis and arced about the second rotational axis,
    wherein the recognition unit has a transmitter configured to transmit radiation having at least one radiation portion in the wavelength range which is at least partially in the infrared spectrum,
    wherein the transmitter unit is configured to transmit radiation in at least one additional wavelength range, and
    wherein the transmitter unit is configured to transmit radiation successively in (a) the wavelength range which is at least partially in the infrared spectrum and (b) in the at least one additional wavelength range.

* * * * *

UNITED STATES PATENT AND TRADEMARK OFFICE
CERTIFICATE OF CORRECTION

PATENT NO. : 8,701,534 B2  Page 1 of 1
APPLICATION NO. : 12/733764
DATED : April 22, 2014
INVENTOR(S) : Visel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 427 days.

Signed and Sealed this

Twenty-ninth Day of September, 2015

Michelle K. Lee
*Director of the United States Patent and Trademark Office*